(12) United States Patent
Bruns et al.

(10) Patent No.: US 8,334,312 B2
(45) Date of Patent: Dec. 18, 2012

(54) FUNGICIDAL MIXTURES FOR WOOD PRESERVATION

(75) Inventors: Rainer Bruns, Leverkusen (DE); Thomas Jaetsch, Köln (DE); Martin Kugler, Leichlingen (DE); Peter Spetmann, Krefeld (DE)

(73) Assignee: LANXESS Deutschland GmbH, Leverkusen (DE)

( * ) Notice: Subject to any disclaimer, the term of this patent is extended or adjusted under 35 U.S.C. 154(b) by 1059 days.

(21) Appl. No.: 11/883,973

(22) PCT Filed: Feb. 1, 2006

(86) PCT No.: PCT/EP2006/000867
§ 371 (c)(1),
(2), (4) Date: Aug. 5, 2008

(87) PCT Pub. No.: WO2006/084615
PCT Pub. Date: Aug. 17, 2006

(65) Prior Publication Data
US 2008/0293793 A1 Nov. 27, 2008

(30) Foreign Application Priority Data
Feb. 12, 2005 (DE) .................. 10 2005 006 420

(51) Int. Cl.
*A01N 43/707* (2006.01)
*A01P 3/00* (2006.01)

(52) U.S. Cl. ....................................................... 514/383

(58) Field of Classification Search .................. None
See application file for complete search history.

(56) References Cited

U.S. PATENT DOCUMENTS

| 4,156,001 A | 5/1979 | Brandes et al. .............. 424/249 |
| 4,542,146 A | 9/1985 | Van Gestel et al. ........... 514/383 |
| 5,223,524 A | 6/1993 | Valcke ........................ 514/383 |
| 6,527,981 B1 * | 3/2003 | Tseng et al. .................. 252/384 |
| 7,691,444 B2 * | 4/2010 | Hayward et al. ......... 427/255.25 |
| 2008/0293793 A1 * | 11/2008 | Bruns et al. .................... 514/383 |

FOREIGN PATENT DOCUMENTS

| EP | 254 857 | 2/1988 |
| WO | 96/01054 | 1/1996 |
| WO | 96/38040 | 12/1996 |
| WO | 97/41727 | 11/1997 |
| WO | 00/71314 | 11/2000 |
| WO | 2004/054766 A1 | 7/2004 |
| WO | WO 2004/054766 * | 7/2004 |
| WO | 2005/063021 | 7/2005 |

OTHER PUBLICATIONS

XP002377208 & CN 1 268 292 A (Jiangsu Nuohua Agric Chem Co Ltd) Oct. 4, 2000.
XP002377209 & NZ 331 830 A (Doyle, J) Sep. 29, 2000.

* cited by examiner

*Primary Examiner* — Shanon A Foley
(74) *Attorney, Agent, or Firm* — Nicanor A. Kohncke

(57) ABSTRACT

Using synergistically effective mixtures comprising triadimefon and/or triadimenol and at least one further known fungicidally active compound, it is possible to protect industrial materials, in particular wood, against attack, damage and/or destruction by biological pests, in particular by wood-destroying fungi.

7 Claims, No Drawings

FUNGICIDAL MIXTURES FOR WOOD PRESERVATION

CROSS REFERENCE RELATED PATENT APPLICATIONS

The present patent application claims the right of priority under 35 U.S.C. §119 (a)-(d) and 35 U.S.C. §365 of International Application No. PCT/EP2006/000867, filed 17 Aug. 2006, which was published in German as International Patent Publication No. WO 2006/084615A1, which is entitled to the right of priority of German Patent Application No. DE 102005006420.5, filed on 12 Feb. 2005.

The present invention relates to the use of synergistically effective fungicidal mixtures comprising triadimefon and/or triadimenol and at least one further known fungicidally active compound for protecting industrial materials, in particular wood, against attack, damage and/or destruction by biological pests, in particular by wood-destroying fungi.

Triadimefon ((±)-1-(4-chlorophenoxy)-3,3-dimethyl-1-(1H-1,2,4-triazol-1-yl)butan-2-one) and triadimenol ((±)-1-(4-chlorophenoxy)-3,3-dimethyl-1-(1H-1,2,4-triazol-1-yl)butan-2-ole) are known fungicides for protecting plants against attack by fungi (cf. DE-A 2552967); however, in the protection of wood, they cannot be employed on their own since there are gaps in the activity spectrum against microorganisms which are of relevance in the protection of wood (cf. EP-A 254857).

Triazole fungicides, such as tebuconazole (cf. EP-A 254857) and propiconazole (cf. U.S. Pat. No. 4,542,146), have already been described for use in the protection of wood; in laboratory tests, their activity on their own is very promising; however, in practice, they do not always ensure sufficient protection of the wood. For this reason, in practice, wood is frequently protected against damage or destruction by wood-destroying fungi using a combination of the two azole fungicides tebuconazole and propiconazole (cf. U.S. Pat. No. 5,223,524).

Although some literature references (cf., for example, WO 00/71314) mention triadimefon or triadimenol as possible mixing partners for various active compounds for protecting wood, these prior-art mixtures are, in many respects, in need of improvement and, owing to the activity gaps mentioned, hitherto do not play any role in the protection of wood. Accordingly, there was still a need for improved biocidal compositions, providing effective protection of industrial materials, in particular wood.

Surprisingly, it has now been found that the combination of triadimefon or triadimenol, which on its own is not effective, with tebuconazole or propiconazole acts synergistically against microorganisms which are of relevance in the protection of wood, i.e. the fungicidal efficacy of the synergistic mixtures is, in an unexpected manner, higher than the sum of the fungicidal efficacies of the fungicides in question on their own.

Accordingly, the present invention provides the use of an active compound mixture comprising a synergistically effective, amount of a) triadimefon and/or triadimenol and b) tebuconazole or propiconazole for protecting industrial materials, in particular wood, against attack, damage and/or destruction by biological pests.

By virtue of the synergistically enhanced activity, the use according to the invention has the additional advantage that, owing to the lower application rate of fungicide in a composition for the protection of wood, not only is an economic advantage achieved, but the safety risk for the environment is also reduced.

The weight ratios of the active compounds a) and b) in the active compound mixture to be used according to the invention can be varied within a relatively wide range. Preferred are weight ratios of tebuconazole or propiconazole to triadimefon and/or triadimenol of from 1:9 to 9:1, particularly preferably from 1:4 to 4:1.

Particularly preferably, the active compound mixtures to be used according to the invention comprise a) triadimefon and b) tebuconazole in a weight ratio of from 3:1 to 1:3.

Likewise particularly preferably, the active compound mixtures to be used according to the invention comprise a) triadimefon and b) propiconazole in a weight ratio of from 3:1 to 1:3.

Furthermore particularly preferably, the active compound mixtures to be used according to the invention comprise a) triadimenol and b) tebuconazole in a weight ratio of from 2:1 to 1:2.

The synergistic mixtures to be used according to the invention have particularly high microbicidal, in particular fungicidal, action, combined with a broad activity spectrum against microorganisms which are of relevance in the protection of materials; they are especially effective against wood-destroying fungi.

By way of example—but not by way of limitation—the following microorganisms may be mentioned:

*Coniophora puteana, Coriolus versicolor, Gloeophyllum abietinum, Gloeophyllum trabeum, Lentinus tigrinus, Poria monticola, Poria placenta, Serpula lacrymans, Stereum sanguinolentum, Tyromyces palustris*

If appropriate, the synergistic mixtures to be used according to the invention can be mixed with a further microbicidal compound c) to widen the activity spectrum or to achieve special effects.

Here, preference is given to using mixtures comprising a synergistically effective amount of a) triadimefon and/or triadimenol and b) tebuconazole or propiconazole and one or more of the following microbicidal components c): dichlofluanid, tolylfluanid, carbendazim, thiabendazole, benzalkonium chloride, fenpropimorph, bethoxazin, 4,5-dichloro-N-octylisothiazolin-3-one, N-octylisothiazolin-3-one, benzisothiazolinone, thiocyanato-methyl-thiobenzothiazole, 3-iodo-2-propynyl n-butylcarbamate, o-phenylphenol, N-(3-aminopropyl)-N-dodecylpropane-1,3-diamine.

Particularly preferred is the use according to the invention of mixtures which, as further component c), comprise tolylfluanid, bethoxazin, benzalkonium chloride, 3-iodo-2-propynyl butylcarbamate or a mixture of these components.

In general, the mixtures to be used according to the invention comprise 0.01-85% by weight of triadimefon and/or triadimenol, 0.01-85% by weight of propiconazole or tebuconazole and 0.05-80% by weight of one or more components c).

Preferably, the mixtures to be used according to the invention comprise 0.1-40% by weight of triadimefon and/or triadimenol, 0.1-40% by weight of propiconazole or tebuconazole and 0.1-30% by weight of tolylfluanid, bethoxazin, benzalkonium chloride, 3-iodo-2-propynyl butylcarbamate or mixtures thereof.

For the use according to the invention, it is possible to convert both the active compound mixture to be used according to the invention and the individual active compounds comprised therein, depending on their respective physical and/or chemical properties, into customary formulations, such as solutions, emulsions, suspensions, powders, foams, pastes, granules, aerosols and microencapsulations in polymeric substances.

The present invention also provides microbicidal compositions comprising a synergistically effective amount of a) triadimefon and/or triadimenol and b) tebuconazole or propiconazole and at least one diluent or solvent, if appropriate further auxiliaries and additives and if appropriate one or more further fungicidal components c).

The formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methyl cellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The microbicidal compositions which can be used for protecting the industrial materials generally comprise the active compound combination in a concentration of from 0.05 to 95% by weight, preferably from 0.2 to 40% by weight and in particular from 0.5 to 25% by weight.

The use concentrations of the active compounds or the active compound combinations to be used depend on the type and the occurrence of the microorganisms to be controlled and on the composition of the material to be protected. The optimum application amounts can be determined by test series. In general, the use concentrations are in the range from 0.001 to 5% by weight, preferably from 0.01 to 1.5% by weight, based on the material to be protected.

With the active compound combinations or compositions to be used according to the invention it is possible, in an advantageous manner, to replace the microbicidal compositions hitherto available by more effective compositions. They have good stability and, in an advantageous manner, a broad activity spectrum.

Wood which can be protected by the active compound mixtures to be used according to the invention or the compositions comprising them, is to be understood as meaning, for example: building timber, wooden beams, railway sleepers, bridge components, boat jetties, wooden vehicles, boxes, pallets, containers, telegraph poles, wood paneling, wooden windows and doors, or wooden products which are used quite generally in house-building or in building joinery. The active compound mixture to be used according to the invention and the compositions comprising it serve in particular for protecting solid wood and wooden products prepared therefrom.

In the use according to the invention of the active compound mixtures, the active compound mixtures can be employed as such or in the form of their individual active compounds. Here, it is possible to convert the active compound mixtures or the individual active compounds comprised therein first into formulations or use forms prepared therefrom, such as ready-to-use solutions, suspensions, pastes, soluble powders.

The use according to the invention for protecting wood is carried out in a customary manner in the context of known processes for treating wood, such as, for example, by spray, paint, dip and large-scale industrial impregnation processes, for example vacuum, double vacuum or pressure processes.

A particularly effective protection of wood is achieved by the use according to the invention in the context of large-scale industrial impregnation processes, such as, for example, vacuum, double vacuum or pressure processes.

The present invention furthermore provides a process for protecting wood, where the wood is sprayed with, painted with or dipped into a synergistically effective amount of a) triadimefon and/or triadimenol and b) tebuconazole or propiconazole and at least one diulent or solvent, if appropriate further auxiliaries and additives and if appropriate one or more fungicidal components c) or preferably, impregnated using a vacuum, double vacuum, pressure or dip process.

The present invention is described with reference to specific details and examples of particular embodiments thereof. It is not intended that such details and examples be regarded as limitations upon the scope of the invention except insofar as and to the extent that the are included in the accompanying claims.

BIOLOGICAL EXAMPLES

Mycelium pieces were punched out of colonies of the wood-destroying organisms *Coriolus versicolor, Poria placenta, Gloeophyllum trabeum* and *Cornophora puteana* and incubated at 26° C. on a malt extract/peptone-containing nutrient agar. Here, the growth of the fungal threads with and without added active compound was compared. The stated minimum inhibitory concentration (MIC) is the active compound concentration at which the radial growth of the fungal threads is suppressed completely.

Using the method described by Kull et al. (F. C. Kull, P. C. Eismann, H. D. Sylvestrowicz, R. L. Mayer, Applied Microbiology 9, 538 to 541, 1961), the synergism was determined. Here, the following relations apply:

$$QA/Qa + QB/Qb = SI$$

Qa=concentration of substance A which is the MIC
Qb=concentration of substance B which is the MIC QA=concentration of substance A in the concentration of A/B which suppresses microbial growth
QB=concentration of substance B in the concentration of A/B which suppresses microbial growth
SI=synergistic index
SI=1 means additivity
SI>1 means antagonism
SI<1 means synergism

EXAMPLE 1

Mixtures Comprising Triadimenol and Tebuconazole

| Fungus | Qa | Qb | QA | QB | SI | Ratio a:b |
|---|---|---|---|---|---|---|
| Poria placenta | 1 | 1 | 0.14 | 0.56 | 0.70 | 1:4 |
|  | 1 | 1 | 0.28 | 0.42 | 0.70 | 2:3 |
|  | 1 | 1 | 0.42 | 0.28 | 0.70 | 3:2 |
| Gloeophyllum trabeum | 1 | 0.7 | 0.1 | 0.4 | 0.67 | 1:4 |
|  | 1 | 0.7 | 0.2 | 0.3 | 0.63 | 2:3 |
|  | 1 | 0.7 | 0.3 | 0.2 | 0.59 | 3:2 | a = triadimenol
b = tebuconazole

EXAMPLE 2

Mixtures Comprising Propiconazole and Triadimefon

| Fungus | Qa | Qb | QA | QB | SI | Ratio a:b |
|---|---|---|---|---|---|---|
| Poria placenta | 1 | 3 | 0.63 | 0.07 | 0.65 | 9:1 |
|  | 1 | 3 | 0.56 | 0.14 | 0.61 | 4:1 |
|  | 1 | 3 | 0.28 | 0.42 | 0.42 | 2:3 |
| Coriolus versicolor | 3 | 6 | 0.8 | 0.2 | 0.30 | 4:1 |
|  | 3 | 6 | 0.5 | 0.5 | 0.25 | 1:1 |
|  | 3 | 6 | 1.2 | 1.8 | 0.70 | 2:3 | a = propiconazole
b = triadimefon

EXAMPLE 3

Mixtures Comprising Tebuconazole and Triadimefon

| Fungus | Qa | Qb | QA | QB | SI | Ratio a:b |
|---|---|---|---|---|---|---|
| Coriolus versicolor | 0.3 | 3 | 0.24 | 0.06 | 0.82 | 4:1 |
|  | 0.3 | 3 | 0.18 | 0.12 | 0.64 | 3:2 |
|  | 0.3 | 3 | 0.07 | 0.63 | 0.44 | 1:9 |
| Gloeophyllum trabeum | 0.5 | 30 | 0.4 | 0.1 | 0.80 | 4:1 |
|  | 0.5 | 30 | 0.25 | 0.25 | 0.51 | 1:1 |
|  | 0.5 | 30 | 0.2 | 0.80 | 0.43 | 1:4 |
| Coniophora puteana | 6 | 30 | 2.7 | 0.3 | 0.46 | 9:1 |
|  | 6 | 30 | 2.4 | 0.6 | 0.42 | 4:1 |
|  | 6 | 30 | 1.2 | 4.8 | 0.36 | 1:4 | a = tebuconazole
b = triadimefon

EXAMPLES OF FORMULATIONS

Example 1

Industrial Concentrate

10% triadimefon, 15% propiconazole, 10% Texanol, 15% ethoxylated castor oil, 15% castor oil sodium salt/sodium dodecylbenzenesulphonate preparation, 35% dimethyl fatty amide

Example 2

Industrial Concentrate

15% tebuconazole, 15% triadimefon, 8% Texanol, 13% castor oil sodium salt/sodium dodecylbenzenesulphonate preparation, 14% fatty acid polyethylene glycol ether ester, 35% dimethyl fatty amide

Example 3

Industrial Concentrate 7.5% triadimenol, 7.5% tebuconazol, 9% castor oil sodium salt/sodium dodecylbenzenesulphonate preparation, 27% ethoxylated castor oil, 49% Texanol

Example 4

Emulsifiable Concentrate 2.5% tebuconazole, 2.5% triadimefon, 3% castor oil sodium salt/sodium dodecylbenzenesulphonate preparation, 27% fatty acid polyethylene glycol ether ester, 65% Texanol

Example 5

Composition for Impregnation 0.2% tebuconazole, 0.1% triadimenol, 15% Worléesol 31A (binder concentrate), 0.8% Additol VXW 4940, 3.0% ethoxylated castor oil, 3.0% Texanol; 77.9% water

Example 6

Composition for Impregnation 0.4% triadimefon, 0.1% tebuconazole, 4.0% alkyd resin, 4.0% Dowanol DPM, 91.5% white spirit

Example 7

Primer 0.1% triadimefon, 0.3% tebuconazole, 0.4% tolylfluanid, 6% Dowanol DPM, 10% alkyd resin, 83.2% white spirit

What is claimed is:
1. A process for protecting wood, comprising:
   treating the wood with a synergistically effective amount of a mixture of a) triadimefon and/or triadimenol and b) tebuconazole or propiconazole,
   wherein the weight ratio of said a) triadimenol and/or triadimefon to b) tebuconazole or propiconazole is from 9:1 to 1:9, and wherein said treating comprises impregnating the wood with the mixture using a spray, paint, vacuum, double vacuum, pressure or dip process.

2. The process according to claim 1, wherein said mixture further comprises at least one further antimicrobially effective component.

3. The process according to claim 1, wherein said treating is performed in the presence of at least one diluent or solvent.

4. The process according to claim 1, wherein said treating is performed further in the presence of auxiliaries and additives.

5. The process according to claim 1, wherein the mixture comprises a) triadimefon and b) tebuconazole in a weight ratio of from 3:1 to 1:3.

6. The process according to claim 1, wherein the mixture comprises a) triadimefon and b) propiconazole in a weight ratio of from 3:1 to 1:3.

7. The process according to claim 1, wherein the mixture comprises a) triadimenol and b) tebuconazole in a weight ratio of from 2:1 to 1:2.

* * * * *